United States Patent [19]

Kontos

[11] 4,261,357

[45] Apr. 14, 1981

[54] CATHETER ASSEMBLY FOR INTERMITTENT INTRAVENOUS MEDICAMENT DELIVERY

[75] Inventor: Stavros B. Kontos, Oakland, N.J.

[73] Assignee: Critikon, Inc., Tampa, Fla.

[21] Appl. No.: 7,137

[22] Filed: Jan. 29, 1979

[51] Int. Cl.³ ............................................ A61M 05/00
[52] U.S. Cl. ................................................ 128/214.4
[58] Field of Search ................ 128/214 R, 214.4, 221, 128/347, 348

[56] References Cited

U.S. PATENT DOCUMENTS

| | | | |
|---|---|---|---|
| 3,774,604 | 11/1973 | Danielsson | 128/214.4 |
| 3,853,127 | 12/1974 | Spademan | 128/214.4 |
| 3,977,400 | 8/1976 | Moorehead | 128/214.4 |
| 4,126,133 | 11/1978 | Schwartz | 128/214.4 |

FOREIGN PATENT DOCUMENTS 575559  4/1924  France ..................... 128/214.4

*Primary Examiner*—Dalton L. Truluck
*Attorney, Agent, or Firm*—Donal B. Tobin

[57] ABSTRACT

An intravenous catheter assembly comprises a catheter with an elongate hollow tube and a hub connected to the tube and having an interior cavity communicating with the lumen of the tube. A needle is slidably positioned in the lumen so that its point protrudes slightly beyond the distal end of the tube, whereas the other end of the needle extends through the hub and sealingly contacts the same so that the hub is effectively closed. A blocking device is contained in the cavity which is adapted to block the entrance of the lumen after the needle is withdrawn from the catheter tube to prevent ready re-insertion of an instrument into the lumen; however, flow of fluids into the lumen is not blocked. The hub includes an access provision to the cavity whereby fluids may be deposited into the cavity for delivery to a patient after the needle has been withdrawn from the catheter tube.

7 Claims, 6 Drawing Figures

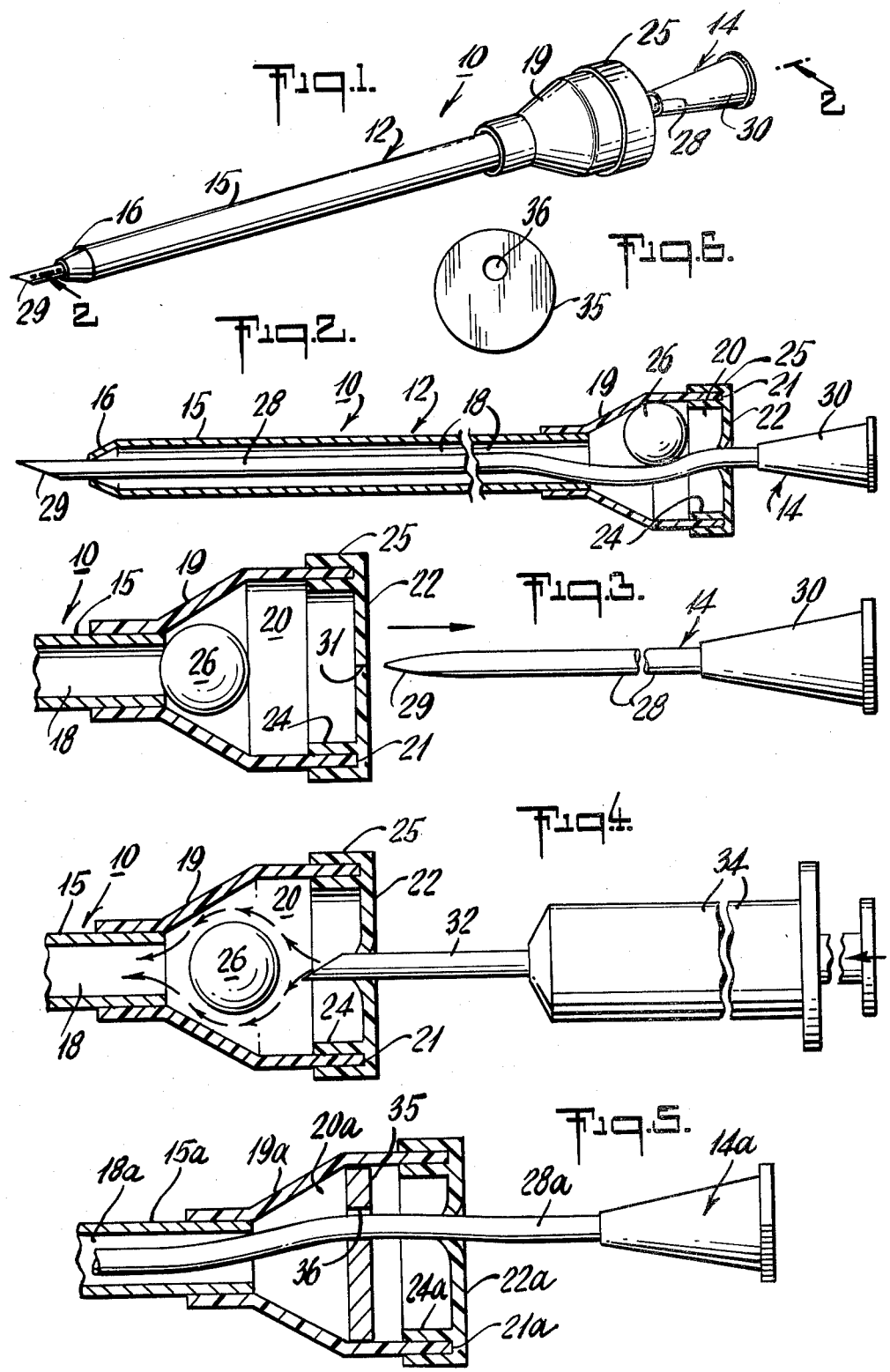

CATHETER ASSEMBLY FOR INTERMITTENT INTRAVENOUS MEDICAMENT DELIVERY

BACKGROUND OF THE INVENTION

The present invention relates to an intravenous catheter assembly, and more particularly, concerns a catheter assembly which is especially useful in situations where medicament is to be delivered in intermittent periods to a patient.

For patients who require periodic intermittent medication by intravenous delivery it is desirable to make one venipuncture, insert an intravenous catheter and leave it in position for periodic use. This procedure, of course, eliminates repetitive piercing of the patient's veins each time he is to receive medication. A catheter of this type whose purpose is to remain in the patient for a prolonged time period generally has to satisfy two requirements: it must prevent blood and/or body fluids from escaping out of the catheter both when being used and during the time period when the catheter is not in use; and it must also have some provision so that the medicament can be deposited through the catheter and into the patient. Various reseal plugs are used in intravenous catheter devices, and are well known for the purpose of preventing the escape of fluids from the catheter in addition to allowing penetration by a needle for delivery of the medicament of the patient. Some typical devices which include this reseal plug or a similar variant are described in U.S. Pat. Nos. 3,585,996; 3,313,299; and 3,097,646. A catheter with a reseal plug generally has the plug, such as a thin rubber diaphragm, covering the open end of the catheter hub. This type of diaphragm is self sealing so that each time the needle makes a puncture through the diaphragm and then is withdrawn after delivering the medication to the patient, the diaphragm seals again to prevent escape of blood or other fluids from the catheter. However advantageous this type of device with reseal plug may be, some problems still arise.

In particular, many catheters which are expected to remain in the patient after initial insertion for periodic use are constructed with plastic catheter tubing. An introducer needle, inside the plastic catheter tube, is used to make the venipuncture, and then the needle is withdrawn leaving the catheter tube in the vein of the patient. The plastic tubing, being generally flexible, minimizes trauma to the patient and does not include the very sharp points and edges such as a metal catheter tubing might have, thereby reducing the risk of damage if the patient should move or roll over the catheter. In this type of catheter with plastic catheter tubing, a problem arises when medication is injected into the hub of the catheter. The attendant or clinician pierces the reseal plug at the hub of the catheter generally with a sharp pointed metal needle at the end of a syringe. If the needle penetrates too far into the catheter its sharp point may, and often times does, puncture the wall of the plastic catheter tube. This, of course, may not only damage the catheter tube but may also leave a hole in the tube so that some of the medication may not be delivered to the patient. Accordingly, while it is still desirable to permit the hypodermic needle to penetrate into the hub of the catheter for delivery of the medication, a means of preventing inadvertent puncture of the catheter tube wall is also being sought. It is to this end and the solution of the problem of puncturing the catheter tube wall that the present invention is directed.

SUMMARY OF THE INVENTION

An intravenous catheter assembly comprises a catheter with an elongate hollow tube and a hub connected to the tube. The hub has an interior cavity communicating with the lumen of the tube. A needle is slidably positioned in the lumen so that its point protrudes slightly beyond the distal end of the catheter tube, the other end of the needle extending through the hub and being in sealing contact therewith so that the hub is effectively closed. Means in the cavity is adapted to block the entrance of the lumen after the needle is withdrawn from the catheter tube to prevent ready reinsertion of an instrument into the lumen, but is adapted to allow flow of fluids into the lumen. The hub includes means for access to the cavity whereby fluids may be deposited into the cavity for delivery to the patient after the needle has been withdrawn from the catheter tube.

In a preferred embodiment of the present invention, the catheter tube is made of a flexible, plastic material and the blocking means is a ball having a diameter greater than the diameter of the lumen but smaller than the cross-sectional dimension of the cavity. These dimensional relationships provide clearance for the needle upon original insertion into the catheter tube but prevent ready re-insertion of the needle into the catheter tube after it has been withdrawn. The ball is movable in the cavity so that fluids injected into the cavity will be permitted to enter into the lumen for delivery to a patient. In this embodiment, the means for access to the cavity is a pierceable, self-sealing diaphragm placed over an open end of the hub. Upon original insertion, the needle pierces the diaphragm; upon withdrawal of the needle, the diaphragm is adapted to sealingly close to prevent escape of fluids from the hub.

In accordance with the principles of the present invention, a significant advantage lies in the blockage of the lumen of the catheter tube to prevent re-insertion of the needle or any like instrument into the catheter tube after the needle has been withdrawn. By preventing the needle from being re-inserted into the lumen of the catheter tube, any damage which could be caused by the sharp point of the needle is avoided, in addition to any loss of fluid medicament should the catheter tube be ruptured by the sharp point of the needle. Further advantages are offered by the present invention as will become more clear when reading the detailed description hereof.

BRIEF DESCRIPTION OF THE DRAWINGS

FIG. 1 is a perspective view illustrating the preferred intravenous catheter assembly of the present invention;

FIG. 2 is a cross-sectional view taken along line 2—2 of FIG. 1;

FIG. 3 is a partial cross-sectional view illustrating the interior of the catheter hub after the introducer needle has been withdrawn;

FIG. 4 is a partial cross-sectional view illustrating the interior of the catheter hub when a needle from a syringe enters the cavity to deliver medicament;

FIG. 5 is a partial cross-sectional view illustrating an alternate blocking means located inside the catheter hub; and FIG. 6 is an elevational view illustrating the blocking device of FIG. 5.

DETAILED DESCRIPTION

While this invention is satisfied by embodiments of many different forms there is shown in the drawings and will herein be described in detail a preferred embodiment of the invention, with the understanding that the present disclosure is to be considered as exemplary of the principles of the invention and is not intended to limit the invention to the embodiment illustrating. The scope of the invention will be pointed out in the appended claims.

Adverting to the drawings, particularly FIGS. 1 and 2, there is illustrated an intravenous catheter assembly 10 particularly useful for periodic or intermittent intravenous medicament delivery. Catheter assembly 10 is comprised of two general components, namely a catheter 12 and an introducer needle 14. Catheter 12 is constructed of an elongate hollow tube 15, preferably slender and smooth surfaced to provide minimal drag and discomfort upon insertion in the patient. Furthermore, to eliminate trauma to the patient and unnecessary rigidity, catheter tube 15 is preferably made of a flexible, plastic material. The distal end 16 of the catheter tube tapers inwardly in order to facilitate venipuncture and subsequent insertion into the patient's vein. The hollow inside portion of the catheter tube forms a lumen 18 through which medicaments pass on the way to the patient.

At or near the proximal end of catheter tube 15 hub 19 is connected. This hub is preferably a female Luer connection which is well known and commonly used as a catheter hub. The hub is formed so that its interior is a cavity 20, and this cavity communicates with lumen 18 in a catheter tube. In most instances, cavity 20 has a much larger cross-sectional dimension than the diameter of lumen 18, in order for the cavity to be able to receive the medicament for eventual delivery to the patient. In hub 19 being described, the end 21 opposite the connection to the catheter tube is an open end, and is covered by a pierceable, self-sealing diaphragm 22. This diaphragm is preferably made of rubber or the like material which will allow a sharp pointed instrument to pierce the material, but which serves to seal itself after the instrument is withdrawn so that no fluids may escape particularly through the hole or slit made by the piercing instrument. It is noted in FIG. 2, that diaphragm 22 includes two annular rims 24 and 25; these rims snugly fit around the wall of hub 19 and may be secured thereto by various means such as adhesives, heat sealing and the like, if desired.

Located inside cavity 20 is a ball 26. Ball 26 is free to move around inside the cavity inasmuch as it has a diameter smaller than the cross-sectional dimension of the cavity. On the other hand, ball 26 has a diameter greater than the diameter of lumen 18. In this regard, the ball cannot enter lumen 18 of the catheter tube, but is confined within the cavity 20 inasmuch as diaphragm 22 serves to effectively enclose the cavity with the ball therein.

Introducer needle 14, the other general component of the present intravenous catheter assembly, includes a long slender needle 28 the distal end 29 of which is pointed. Needle 28 may or may not be hollow depending upon choice of the fabricator. The opposite end of introducer needle 14 has a knob 30 which facilitates gripping by the operator in order to be able to manipulate the needle.

Referring particularly to FIG. 2, catheter assembly 10 is illustrated in the relative positions of introducer needle 14 and catheter 12 upon being originally fabricated. It can be seen that needle 28 is slidably positioned in lumen 18 of the catheter tube, and that the distal pointed end 29 of the needle protrudes slightly beyond distal end 16 of the catheter tube. This, of course, facilitates venipuncture inasmuch as the point of the needle is the leading element in this procedure. In order to become positioned in lumen 18, the point of the needle has had to pierce diaphragm 22. It should be pointed out that when needle point 29 pierces diaphragm 22 it is not attached to hub 19 nor is ball 26 in cavity 20. After the needle has pierced the diaphragm and is inserted into lumen 18, ball 26 is positioned in the cavity, and then the diaphragm is sealed to the hub. As seen in the drawings, the proximal end of the needle extends beyond the open end of the tube, so that the knob can be easily grasped. In this completed package, ball 26 usually presses against the slender needle and may even tend to slightly bend the needle barrel; this presents no permanent distortion inasmuch as the bend is slight and the needle is generally somewhat resilient. The catheter assembly, in the configuration illustrated in FIG. 2, is used to effect venipuncture so that catheter tube 15 may be properly positioned in the vein of the patient. Once in proper position, introducer needle 14 is gripped by its knob 30 and slowly withdrawn from the catheter while leaving catheter tube 15 in the patient. FIG. 3 of the drawings illustrates especially the interior of the catheter hub after intorducer needle 14 has been withdrawn.

It can be seen that, once the needle is completely removed from the catheter, the slit formed by the piercing needle closes due to the self-sealing characteristics of the diaphragm. This seal is important to prevent blood from flowing through catheter tube 15 and out of hub 19. Thus, the catheter may now remain in the patient and be used for periodic delivery of medicament. It is noted when viewing FIG. 3, that ball 26 remains freely movable in cavity 20.

When it is time to use the catheter for delivering medicament to the patient, the operator merely pierces diaphragm 22 with the needle 32 of an appropriate syringe 34 or like device carrying the fluid medicament. This procedure is illustrated in FIG. 4. Once needle 32 passes through the diaphragm into the cavity, it encounters ball 26. The ball effectively blocks ready entrance by the hypodermic needle into lumen 18 of the catheter tube. Thus, the point of needle 32 will penetrate no further than cavity 20; moreover, this blockage can be felt by the operator to provide a clear indication that the needle is in the proper position for depositing the medicament. Once the fluid medicament flows out of needle 32 when in the cavity, it will flow around the ball and into lumen 18 of the catheter tube for eventual passage into the patient. Fluid flow motion in addition to the movability of the ball allows the fluid medicament to flow around the ball and into the lumen of the tube. When the injection is complete, needle 32 is withdrawn and the diaphragm once again self seals, closing the hub and preventing any backflow of blood or fluids out of the catheter. It can be seen that not only is periodic delivery of medicament provided in this invention, but damage to the preferably plastic catheter tube is also eliminated by keeping the point of the hypodermic needle away from the plastic tube.

It is to be appreciated that other blocking devices may be incorporated in the cavity of the hub to serve the same purpose as the ball. For example, one alternate embodiment is illustrated in FIGS. 5 and 6. Instead of a ball, the blocking means in cavity 20a is a disc-like insert 35 with a hole 36 therethrough offset from the center of the insert.

Insert 35 is preferably movable within cavity 20a, but may be fixed to the inside surface of hub 19a in order to be stationary, if desired. During fabrication of the catheter assembly, needle 28a pierces diaphragm 22a and is then carefully inserted through hole 36 in insert 35, whereupon the needle then is slidably positioned in lumen 18a. It is seen that the offset hole in the insert causes a slight bending of the needle when originally inserted into the lumen. This bend is not a problem, and serves to indicate the difficulty to be encountered upon subsequent re-insertion of the needle. Diaphragm 22a is then sealed to hub 19a. Insert 35 performs its function substantially as described in the above embodiment; once the introducer needle has been withdrawn, especially when insert 35 is movable in the cavity, re-introduction of any needle into the cavity would encounter the insert which blocks entrance to the lumen. The chances of blindly locating hole 36 in the insert are very small due to the offset nature of the hole. Accordingly, the medicament needle is effectively prevented from entering the lumen of the catheter tube.

There are some instances when the catheter assembly is used without an introducer needle which is to be withdrawn after venipuncture. In that case, an elongate hollow needle having a pointed distal end replaces the catheter tube as described hereinbefore. The hub is directly connected to the hollow needle, with the blocking means and its various features being the same as previously described. Venipuncture is effected merely by inserting the hollow needle, generally a rigid, smooth surfaced metal, into the vein of the patient.

Thus, the present invention provides a catheter assembly for intermittent intravenous medicament delivery which advantageously protects the catheter tube from being damaged by the sharp point of the hypodermic needle which carries the medicament for the patient.

What is claimed is:

1. An intravenous catheter assembly comprising: a catheter comprised of an elongate hollow tube and a hub connected at one end of said tube, the other end of said hub being an open end, said hub having an interior cavity communicating with the lumen of said tube; a needle slidably positioned in the lumen of the tube, the distal, pointed end of the needle adapted to protrude slightly beyond the distal end of said catheter tube, the proximal end of said needle extending beyond said open end of said hub; blocking means movably disposed and completely contained within said cavity adapted to automatically block the entrance of said lumen after said needle is withdrawn from the catheter tube to prevent ready re-insertion of an instrument into said lumen but adapted to allow flow of fluids into said lumen; and separate means covering said open end of the hub to prevent fluid from flowing out of the hub after said needle has been withdrawn, said covering means adapted to provide access to said cavity whereby fluids may be deposited into said cavity for delivery to a patient after said needle has been withdrawn from the catheter tube.

2. An intravenous catheter assembly as defined in claim 1 wherein said covering means is a pierceable self-sealing diaphragm over the open end of sad hub, said diaphragm being pierced by said needle upon original insertion of the needle into the catheter, and adapted to sealingly close after the needle has been withdrawn.

3. An introducer catheter assembly as defined in claim 1 wherein said catheter tube is made of flexible, plastic material.

4. An intravenous catheter assembly comprising: a catheter comprised of an elongate hollow tube and a hub connected to said tube having an interior cavity communication with the lumen of the tube; a needle slidably positioned in said lumen so that its point protrudes slightly beyond the distal end of the catheter tube, the other end of said needle extending through said hub and being in sealing contact therewith so that said hub is effectively closed; means movably disposed and completely contained within said cavity adapted to automatically block the entrance of said lumen after said needle is withdrawn from the catheter tube to prevent ready re-insertion of an instrument into the lumen but adapted to allow flow of fluids into the lumen; said hub having means for access to said cavity whereby fluids may be deposited into said cavity for delivery to a patient after said needle has been withdrawn from the catheter tube.

5. An intravenous catheter assembly comprising: a catheter comprised of an elongate hollow tube and a hub connected at one end of said tube, the other end of said hub being an open end, said hub having an interior cavity communicating with the lumen of said tube; a needle slidably positioned in the lumen of the tube, the distal, pointed end of the needle adapted to protrude slightly beyond the distal end of said catheter tube, the proximal end of said needle extending beyond said open end of said hub; a ball having a diameter greater than the diameter of said lumen but smaller than the cross-sectional dimension of said cavity so that the ball may provide clearance for the needle upon original insertion but prevent ready re-insertion of an instrument into the catheter tube after the needle has been withdrawn, said ball being movable in said cavity so that fluid injected into said cavity will be permitted to enter said lumen for delivery to a patient; and means covering said open end of the hub to prevent fluid from flowing out of the hub after said needle has been withdrawn, said covering means adapted to provide access to said cavity whereby fluids may be deposited into said cavity for delivery to a patient after said needle has been withdrawn from the catheter tube.

6. An intravenous catheter assembly comprising: a catheter comprised of an elongate hollow tube and a hub connected at one end of said tube, the other end of said hub being an open end, said hub having an interior cavity communicating with the lumen of said tube; a needle slidably positioned in the lumen of the tube, the distal, pointed end of the needle adapted to protrude slightly beyond the distal end of said catheter tube, the proximal end of said needle extending beyond said open end of said hub; a disc-like insert with a hole therethrough offset from its center, said needle being inserted through said hole upon its original insertion into the catheter, said offset hole serving to prevent ready re-insertion of an instrument into the catheter tube after the needle has been withdrawn, but permitting fluids injected into said cavity to enter said lumen for delivery to a patient; and means covering said open end of the hub to prevent fluid from flowing out of the hub after said needle has been withdrawn, said covering means adapted to provide access to said cavity whereby fluids may be deposited into said cavity for delivery to a patient after said needle has been withdrawn from the catheter tube.

7. An intravenous catheter as defined in claim 6 wherein said disc-like insert is fixedly disposed in said cavity.

* * * * *